(12) United States Patent
Campbell

(10) Patent No.: US 6,638,303 B1
(45) Date of Patent: Oct. 28, 2003

(54) HEART VALVE PROSTHESIS

(75) Inventor: Louis A. Campbell, Austin, TX (US)

(73) Assignee: Carbomedics, Inc., Austin, TX (US)

( * ) Notice: Subject to any disclaimer, the term of this patent is extended or adjusted under 35 U.S.C. 154(b) by 0 days.

(21) Appl. No.: 09/665,306

(22) Filed: Sep. 19, 2000

Related U.S. Application Data

(63) Continuation-in-part of application No. 09/042,372, filed on Mar. 13, 1998, now abandoned.

(51) Int. Cl.[7] ................................................. A61F 2/24
(52) U.S. Cl. ..................................................... 623/2.2
(58) Field of Search ................................ 623/2.2, 2.22, 623/2.26, 2.25, 2.27, 2.28, 2.3, 2.33

(56) References Cited

U.S. PATENT DOCUMENTS

| | | | | |
|---|---|---|---|---|
| 3,974,854 A | * | 8/1976 | Kurpanek | 137/512 |
| RE30,507 E | * | 2/1981 | Kaster | 3/1.5 |
| 4,363,142 A | | 12/1982 | Meyer | 3/1.5 |
| 4,605,408 A | | 8/1986 | Carpentier | 623/2 |
| 4,657,545 A | | 4/1987 | Zibelin | 623/2 |
| 4,689,046 A | | 8/1987 | Bokros | 623/2 |
| 4,692,165 A | | 9/1987 | Bokros | 623/2 |
| 4,979,955 A | | 12/1990 | Smith | 623/2 |
| 5,135,538 A | | 8/1992 | Pawlak et al. | 623/2 |
| 5,554,184 A | | 9/1996 | Machiraju | 623/2 |
| 5,814,100 A | | 9/1998 | Carpentier et al. | 623/2 |
| 5,961,550 A | | 10/1999 | Carpentier et al. | 623/2 |
| 6,039,759 A | | 3/2000 | Carpentier et al. | 623/2 |

FOREIGN PATENT DOCUMENTS

| | | | |
|---|---|---|---|
| DE | 3128-704 A1 | 7/1981 | |
| EP | 121-473 A | 3/1984 | A61F/1/22 |
| WO | 97/30658 | 8/1997 | A61F/2/24 |

OTHER PUBLICATIONS

Lee, Chong–Sun; Aluri, Srinivas; Chandran, Krishnan B.; *Effect of Valve Holder Flexibility on Cavitation Initiation with Mechanical Heart Valve Prostheses*; Jan. 1996, *Journal of Heart Valve Disease*, 5(1), pp. 104–113.

Dexter, Elisabeth U.; Aluri, Srinivas; Radcliffe, Robert R.; Zhu, Hong; Carlson, David D.; Heilman, Troy E.; Chandran, Krishnan B.; Richenbacher, Wayne E.; *In Vivo Demonstration of Cavitation Potential of a Mechanical Heart Valve*; May 1998, *Asaio Journal.* (Sep.–Oct. 1999) 45 (5), pp. 436–441.

Chandran, K.B.; Dexter, E. U.; Aluri, S.; Richenbacher, W. E.; *Negative Pressure Transients with Mechanical Heart–Valve Closure: Correlation Between In Vitro and In Vivo Results*; 1998, *Annals of Biomedical Engineering*, vol. 26, pp. 546–556.

Chandran, Krishnan Bala; Aluri, Srinivas; *Mechanical Valve Closing Dynamics: Relationship Between Velocity of Closing, Pressure Transients, and Cavitation Initiation*; *Annals of Biomedical Engineering*, (Nov.–Dec. 1997) 25 (6), pp. 926–938.

(List continued on next page.)

*Primary Examiner*—Bruce Snow
(74) *Attorney, Agent, or Firm*—Williams, Morgan & Amerson, P.C.; Timothy L. Scott

(57) ABSTRACT

A heart valve prosthesis includes an annular body that has a fluid passageway and at least one rigid leaflet that is pivotally mounted in the passageway of the body. The leaflet is movable between a closed position wherein the fluid passageway is substantially closed and an open position wherein the fluid passageway is not substantially closed. The heart valve prosthesis has a biasing mechanism that is connected to the body and leaflet and is configured to exert a force on the leaflet to move the leaflet to the closed position before a second fluid pressure exerted on an outflow surface of the leaflet exceeds a first fluid pressure exerted on an inflow surface of the leaflet.

10 Claims, 7 Drawing Sheets

OTHER PUBLICATIONS

Brodeur, Michael T., M.D., C.M.; Sutherland, Donald W., M.D.; Koler, Robert D., M.D.; Starr, Albert, M.D.; Kimsey, Jean A., B.S.; Griswold, Herbert E., M.D.; *Red Blood Cell Survival in Patients with Aortic Valvular Disease and Ball–Valve Prostheses*; Oct. 1965, Circulation, vol. XXXII, pp. 570–581.

Rubinson, Richard M., M.D.; Morrow, Andrew G., M.D.; Gebel, Peter, M.D.; *Mechanical Destruction of Erythrocytes by Incompetent Aortic Valvular Prostheses; American Heart Journal*, Feb. 1966, pp. 179–186.

Nevaril, Charles G.; Lynch, Edward C.; Alfrey, Clarence P., Jr.; Hellums, J. David; *Erythrocyte Damage and Destruction Induced by Shearing Stress*; May 1968, *Journal of Laboratory and Clinical Medicine*, pp. 784–790.

Williams, A. R.; *Viscoelasticity of the Human Erythrocyte Membrane; Biorheology*, 1973, vol. 10, pp. 313–319.

Stein, Paul D.; Sabbah, Hani N.; *Measured Turbulence and Its Effect on Thrombus Formation; Circulation Research*, vol. 35, Oct. 1974, pp. 608–614.

Figliola, R.S.; Mueller, T.J.; *On the Hemolytic and Thrombogenic Potential of Occluder Prosthetic Heart Valves From In–Vitro Measurements; Journal of Biomechanical Engineering*, May 1981, vol. 103, pp. 83–89.

Sallam, Ahmed M.; Hwang, Ned H.C.; *Human Red Blood Cell Hemolysis in a Turbulent Shear Flow: Contribution of Reynolds Shear Stresser; Biorheology*, 21, 1984, pp. 783–797.

Hanle, D.D.; Harrison, E.C.; Yoganathan, A.P.; Allen, D.T.; Corcoran, W. H.; *In Vitro Flow Dynamics of Four Prosthetic Aortic Valves: A Comparative Analysis; Journal of Biomechanics*, vol. 22, No. 67, 1989, pp. 597–607.

Giersiepen, M.; Wurzinger, L.J.; Optiz, R.; Reul, H.; *Estimation of Shear Stress–Related Blood Damage in Heart Valve Prostheses—in vitro Comparison of 25 Aortic Valves*; 1990, pp. 300–306.

Lamson, Theodore C.; Frangos, John A.; Deutsch, Steven; Geselowitz, David B.; Tarbell, John M.; *Blood Damage in Regurgitant Flow Through a Closed Prosthetic Heart Valve, Bioprocess Engineering Symposium—1992*, BED–vol. 23, pp. 13–17.

Rand, R. P.; *Mechanical Properties of the Red Cell Members, Biophysical Journal*, vol. 4, 1964, pp. 303–316.

Bull, B.S.; Rubenberg, M. L.; Dacie, J.V.; Brain, M.C.; *Microangiopathic Haemolytic Anaemia: Mechanisms of Red–Cell Fragmentation: in Vitro Studies; Brit. J. Haemat.*, 1968, pp. 643–652.

Sallam, A.M.; Hwang, N.H.C.; *Turbulent Strain Rate and Red Blood Cell Hemolysis*; $36^{th}$ ACEMB, Sep. 1983, p. 80.

* cited by examiner

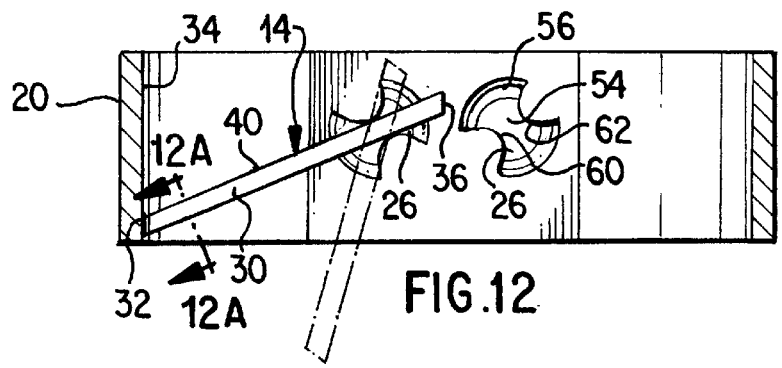
FIG. 12
FIG. 12A
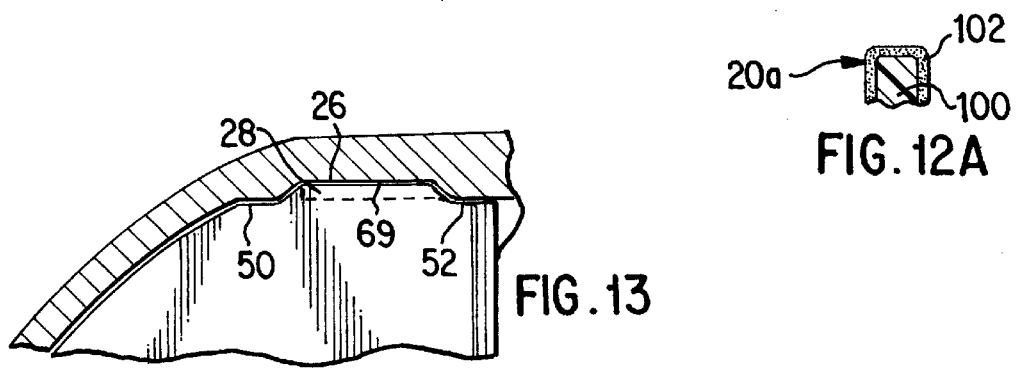
FIG. 13
FIG. 15
FIG. 14
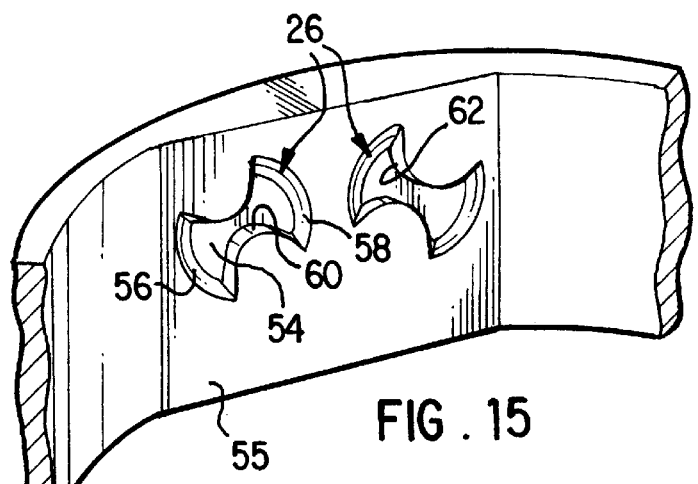
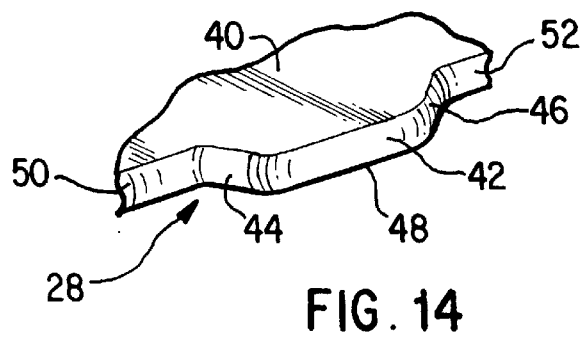

HEART VALVE PROSTHESIS

The present application is a continuation-in-part of co-pending U.S. patent application Ser. No. 09/042,372, filed Mar. 13, 1998, now abandoned the entire text of which is specifically incorporated by reference herein.

BACKGROUND OF THE INVENTION

The invention relates to a heart valve prosthesis, used to replace diseased natural heart valves, and more particularly to a mechanical heart valve prosthesis that uses one or more naturally-operating pivoting members.

Various types of heart valve prostheses have been developed which operate hemodynamically as a result of the pumping action of the heart in which they generally function as check valves. These prosthetic valves fall generally into two categories: "mechanical" valves, comprising relatively rigid leaflets formed of a stiff, biocompatible substance such as pyrolitic carbon; and "bioprosthetic" valves, comprising flexible leaflets often formed of a biological material such as bovine pericardial tissue. One popular design for a mechanical heart valve prosthesis includes an annular valve body in which a pair of opposed leaflet occluders are pivotally mounted. The occluders move between a closed, mated position, blocking blood flow in an upstream direction, thereby minimizing regurgitation, and an open position, allowing blood flow in a downstream direction.

Typically, after receiving a mechanical heart valve prosthesis, the recipient must take chronic anticoagulation treatment for the rest of their life to prevent blood clots. These blood clots are referred to as thrombosis if they adhere to the heart valve. If the clots float away from the valve where they can occlude blood flow to another part of the body, the clots are referred to as thromboembolism. Thrombosis, thromboembolism, and bleeding that results from the drugs that are used to reduce cases of thrombosis and thromboembolism are the most serious problems faced by heart valve recipients. In contrast, after receiving a biological heart valve, the recipient typically only needs the chronic anticoagulation therapy for about ninety days while the sewing ring heals over.

To explain why blood clots occur more frequently in mechanical valve prostheses, scientists often look to the teachings of Verchow, an important nineteenth century scientist, who believed that clotting of the blood, or thrombosis, was the result of three interacting variables. These variables, often referred to as Verchow's triad, include: (1) the susceptibility of a patient's blood to clot formation; (2) foreign material response; and (3) flow conditions.

The susceptibility of a patient's blood to clot formation can be diagnosed to a limited extent. Patients with particular susceptibility to clot formation may require anticoagulation even without the added risk of a prosthetic heart valve to avoid atrial and peripheral thrombosis. However, in the absence of anticoagulation treatment, mechanical valves generally give rise to greater clotting problems than bioprosthetic valves.

According to Verchow, areas of stasis, or low flow, are the most likely accumulation points for clots. For this reason, clots in prosthetic valves usually occur at the point where the sewing ring joins other valve members, or in low flow regions near struts and pivot points. Considerable effort has been directed at eliminating these low flow regions as discussed in U.S. Pat. Nos. 5,147,390 and 5,192,313. Although such attention to flow is likely to reduce the chance of valvular thrombosis, it does not explain the cause for heightened sensitivity to clot formation. Most tissue valves have many areas of blood stasis that are much worse than the pivots and struts in mechanical heart valves yet thrombosis is much less likely to occur in tissue valves than in mechanical valves, in the absence of anticoagulation therapy.

Since low flow does not explain the clotting risk difference between tissue and mechanical valves, a great deal of work has gone into investigating high flow rate effects on blood. High flow rates have been shown to cause damage to blood and to activate clotting mechanisms. In particular, high wall shear stress occurs where a rapidly moving flow meets an immobile boundary, like the walls of a heart valve or blood vessel. This high wall shear stress can cause blood damage. Michael T. H. Brodeur, M. D., et al., Red Blood Cell Survival In Patients With Aortic Valvular Disease and Ball-Valve Prostheses, XXXII Circulation 570 (1995); Richard M. Rubinson, M. D., et al., Mechanical Destruction of Erythrocytes By Incompetent Aortic Valvular Prostheses-Clinical, Hemodynamic, And Hematologic Findings, Am. Heart J. 179 (February 1966); Charles G. Nevaril, et al., Erythrocyte Damage And Destruction Induced By Shearing Stress, J. Lab & Clin. Med. 784 (May 1968).

Damage to the blood can also be caused by a rapid change in blood velocity, even in the absence of an impinging wall, particularly if the flow is turbulent. A. R. Williams, Viscoelasticity Of The Human Erythrocyte Membrane, 10 Biorheology 313–19 (1973); Paul D. Stein and Hani N. Sabbah, Measured Turbulence And Its Effects On Thrombus Formation, 35 Circulation Research 608–14 (1974); R. S. Figliola and T. J. Mueller, On The Hemolytic And Thrombogenic Potential Of Occluder Prosthetic Heart Valves From In-Vitro Measurements, 103 Journal of Biomechanical Eng'g. 83–89 (1981); Ahmed M. Salam and Ned Hwang, Human Red Blood Cell Hemolysis In A Turbulent Shear Flow: Contribution Of Reynolds Shear Stresses, 21 Biorheology 783–797 (1984); L. J. Worzinger, et al., Platelet And Coagulation Parameters Flowing Millisecond Exposure To Laminar Shear Stress, 381–386.

Laser doppler anemometry has been used to measure the forward flow dynamics in various mechanical and tissue valves. D. D. Hanle, et al., Invitro Flow Dynamics Of Four Prosthetic Aortic Valves: A Comparative Analysis, 22 J. Biomechanics 597–607 (1989). The data from these studies has been used to estimate the shear stress related blood damage that occurs during forward flow. M. Giersiepen, et al., Estimation Of Shear Stress-Related Blood Damage In Heart Valve Prostheses-Invitro Comparison Of 25 Aortic Valves, 13 Int'l. J. of Artificial Organs 306–330 (1990). In these reports, the shear stress and estimated damage to blood components with tissue valves is greater than the damage estimated from modern bileaflet mechanical valves during forward flow. The most recent reference even provides clinical comparative data supporting the fact that more hemolysis (risk of thrombosis) is indicated with tissue valves than with mechanical valves. There is also no evidence to suggest small valves are more prone to clotting than large valves, but both wall shear stresses and Reynolds normal stress are much higher in small valves than in large valves. These facts taken together indicate hemolysis is not a good indicator of the increased risk of clot formation with clinical valves, and the differences between the thromboembolic potential of tissue and mechanical valves is not related to forward flow dynamics.

Another possible link between clotting and flow conditions is the existence of high wall stresses or Reynolds normal stress associated with reverse flow leakage after the valve closes. Reynolds stresses on the order of 20,000 to 60,000 dynes/cm2 have been observed within the regurgitate jets occurring through a Bjork-Shiley valve mounted in a Penn-State heart. Baldwin, J. T., et al., Estimation Of Reynolds Stresses Within The Penn State Left Ventricular Assist Device, 36 ASAIO Trans. M274–M278 (1990); Baldwin, J. T., et al., Mean Velocities And Reynolds Stresses Within Regurgitant Jets Produced By Tilting Disk Valves, 37 ASAIO Trans. M351–M353 (1991). The peak Reynolds normal stresses during forward flow are on the order of 1,000 to 4,500 dynes/cm2, much lower than the Reynolds stresses during flow leakage. These higher stresses during leakage flow could be causing activation of the clotting system but high velocity jets are not unique to mechanical heart valves. Biological heart valves are often designed with a small leak in the center of the valve that results in a high velocity jet. Further, as biological valves degrade jets are created at tears and small holes that progress to complete valvular incompetence. If the high velocity leakage jets were a significant cause of activation then biological valves with central leakage would have a higher risk of clotting then biological valves without these jets but no such correlation exists. Also, if such jets were a primary cause of activation there would be an increased risk of clot formation as biological valves failed but this has not been reported.

Wall shear stress inside the pivots is another possible cause of blood damage. Empirical testing methods to determine the wall shear stress inside a heart valve pivot have not been developed but computational methods allow us to estimate these forces. In computational fluid dynamic (CFD) analysis of pivots exposed to pressure gradients of 120 mm of mercury, the flow inside the pivot has been characterized. This flow is laminar rather than turbulent and the wall shear stresses are below 300 dynes/cm2.

The extent of damage to the blood is also dependent on the surface roughness of the immobile surface and perhaps the surface chemistry of the impinging surface. Rougher surfaces are generally associated with increase thrombosis risk but polished pyrolitic carbon, titanium and cobalt chromium alloys used to fabricate mechanical heart valves are much smoother than the biological tissue used to fabricate tissue heart valves. In terms of surface chemistry, the glutaraidehyde treated tissue used to construct most tissue heart valves is toxic to some cells in the blood. Pyrolitic carbon, used for most mechanical heart valves has in contrast been shown to elicit a benign response allowing a confluent layer of protein absorption that is thought to be very non-thrombogenic.

Despite the foregoing evidence, which suggests that, according to Virchow's theory, mechanical valves should be less thrombogenic than tissue valves, the clinical advantage of tissue valves compared to mechanical valves in terms of thrombogenicity is undisputed. Most recently, a study conducted by a group of surgeons and cardiologists in Aahurs, Denmark showed thirty-eight out of forty patients receiving the mostly widely used mechanical valve (St. Jude) had a measurable increased risk of thrombosis as compared to patients receiving tissue valves.

Recently experiments have been conducted which indicate that during the pumping cycle of the heart, mechanical valves experience rapid, relatively high magnitude pressure changes on the upstream or inlet side of the valve. In particular, immediately following the closure of the valve leaflets, rapid, short duration decreases in local pressure on the order of 750 mmHg have been measured. Accordingly, as used herein, the term "pressure transient" refers to a rapid, relatively large (>50 mmHg) pressure change of short duration (<0.1 sec) at a point immediately upstream of the valve inlet at the moment of valve closure. Because the pressure is falling during these pressure changes, they are also referred to as "negative pressure transients." Significantly, tissue valves have not been show to experience negative pressure transients.

In one series of experiments involving negative pressure transients, tissue valves and mechanical valves with pressure transducers adjacent to the valves were implanted into sheep. Negative pressure transients on the order of 750 mmHg were measured upon valve closure with mechanical valves having pyrolytic carbon leaflets. In contrast, the magnitude of the negative pressure change with biological valves was less than 50 mmHg. Although outside the scope of Verchow's theory, there has been work that indicates exposure of blood to rapid pressure transients can cause activation of blood leading to thrombosis. I believe the principle cause of thrombosis in mechanical heart valves is the result of the pressure transient that exists with mechanical valves but is absent with tissue valves. This invention is directed at elimination or at least reduction of this pressure transient by moving the valve to a closed position before the blood is exposed to substantial pressure gradients.

Without being bound by any particular theory, it is believed that the negative pressure transients experienced by most mechanical heart valves occurs as follows. During the closing cycle of a typical mechanical heart valve having pyrolytic carbon leaflets, the volume of blood backflowing through the valve decreases as more of the fluid passageway is occluded by the closing leaflets. However, the velocity (and thus kinetic energy) of the remaining blood backflowing through the valve actually increases as the passageway area decreases. Thus, for a typical bileaflet valve, immediately prior to complete valve closure an extremely high-velocity backflow jet exists at the periphery of the valve leaflets. When the leaflets close fully, the kinetic energy (inertia) of this jet cause it to continue to backflow for a small time interval, resulting in a highly localized negative pressure transient as the small volume of blood is decelerated and stopped. This negative pressure transient can cause a viscoelastic expansion of blood cells, releasing granular material through the cell walls and resulting in an increase in the risk of thrombosis. In extreme cases the cells can be torn, releasing substantial quantities of thrombogenic granular material.

It has previously been suggested in published PCT application number WO/30658 to use magnetic forces in a heart valve assembly to move the leaflets to an equilibrium position that is between the open and closed positions when a zero pressure gradient exists across the valve. As taught by this reference, the purpose in doing this is to minimize the distance the leaflet must travel from this equilibrium position to both the open and closed position, and also to reduce reflux. WO/30658, however, does not recognize or discuss the importance of the exposure of blood to pressure transients, and the device described therein does not achieve the objective of reducing or eliminating the exposure of blood to such closing pressure transients. In fact, an equilibrium position that is between the open and closed positions ensures that the blood will be exposed to global pressure transients of a magnitude sufficient to cause blood flow reversal. As indicated in the publication, both opening and closing of the valve will always take place in two steps, the first being under the influence of magnetic forces, and the second being under the influence of hydraulic forces that result from a global pressure transient.

To the contrary the valve of the present invention substantially eliminates the exposure of blood to closing pressure transients by using a biasing force, such as a mechanical or magnetic force, to move the valve to the closed position when a zero pressure gradient exists across the valve. Moving the valve to a closed position will substantially eliminate the exposure of blood to a closing pressure transient, and therefore, will reduce the risk of thrombosis. The present invention has the further advantage of substantially eliminating closing volume reflux, resulting in a more efficient valve that more closely mimics the performance of a natural heart valve.

SUMMARY OF THE INVENTION

In general, in one aspect, the invention features a heart valve prosthesis. The prosthesis includes an annular body that has a fluid passageway through it and at least one rigid leaflet that is pivotally mounted in the passageway of the body. The leaflet is movable between a closed position in which the fluid passageway is substantially closed and an open position in which the fluid passageway is not closed. A biasing mechanism that is connected to the body and the leaflet exerts a biasing force to bias the leaflet to the closed position. The leaflet is configured to move to the open position when a first fluid pressure exerted on an inflow surface of the leaflet exceeds the biasing force. It is also configured to return to the closed position sooner than prior art valves, preferably before a second fluid pressure exerted on an outflow surface of the leaflet exceeds the first fluid pressure, in contrast to existing art valves that close only after flow reverses and the pressure from a second fluid force on the outflow side of the valve exceeds the first pressure force.

An advantage of the present invention is that the prosthetic valve will fully close under a very low closing pressure transient, thereby reducing damage to blood. In preferred embodiments, the negative pressure transient is reduced to 700 mmHg or less, more preferably to 500 mmHg or less, even more preferably to 250 mmHg or less, and more preferably still to 100 mmHg or less. The valve closes slowly during deceleration of forward flow, thereby minimizing the noise made by the valve that frequently annoys valve recipients. Since the valve will close earlier in the cardiac cycle than prior art valves, the present invention will also substantially reduce or eliminate the closing volume or energy loss associated with retrograde blood flow that results with valves that depend on a flow reversal to close the valve.

As indicated, the mechanism of the invention may be configured to move the leaflet to the closed position when the first fluid pressure is insufficient to overcome the magnetic or mechanical biasing force that is holding the valve closed. The mechanism may include a first magnet that is mounted to the leaflet and a second magnet that is mounted to the orifice body or in the space between the orifice body and stiffening ring or sewing ring. The first and second magnets may be configured to attract each other when the leaflet is in the closed position. The first and second magnets may be configured to repel each other when the leaflet is in the open position. The open position may define a predetermined maximum angular position of the leaflet, and the first and second magnets may be configured to prevent the leaflet from traveling substantially beyond the open position. Alternatively, instead of magnets, the valve prostheses may include a spring. The heart valve prosthesis may be a mechanical bileaflet heart valve prosthesis.

In general, in another aspect, the invention features a heart valve prosthesis that includes an annular body that has a fluid passageway and at least one leaflet that is pivotally mounted in the passageway of the body and is movable between a closed position in which the fluid passageway is closed and an open position in which the fluid passageway is not closed. The heart valve prosthesis also includes a first biasing element mounted to the leaflet and a second biasing element mounted to the body. The second biasing element is configured to interact with the first biasing element to exert a force on the leaflet to move the leaflet to the closed position before the valve experiences a negative pressure transient of 700 mmHg. More preferably, the leaflet is moved to the closed position before the valve experiences a negative pressure transient of 500 mmHg. Even more preferably, the leaflet is closed before the valve experiences a negative pressure transient of 250 mmHg. More preferably still, the leaflet is closed before the valve experiences a negative pressure transient of 100 mmHg. It is also preferred that the leaflet be moved to the closed position before a second fluid pressure exerted on an outflow surface of the leaflet exceeds a first fluid pressure exerted on an inflow surface of the leaflet.

In general, in another aspect, the invention features a method for use with a heart valve prosthesis that has a fluid passageway and at least one leaflet that is located in the passageway and that is similarly movable between a closed position in which the fluid passageway is substantially closed and an open position in which the fluid passageway is not substantially closed. The method includes mounting a biasing element on the leaflet and applying magnetic force to the element to force the leaflet to the closed position before a second fluid pressure exerted on an outflow surface of the leaflet exceeds a first fluid pressure exerted on an inflow surface of the leaflet.

In general, in another aspect, the invention features a method for use with a heart valve prosthesis that has a fluid passageway and at least one leaflet that is located in the passageway and that is similarly movable between a closed position in which the fluid passageway is substantially closed and an open position in which the fluid passageway is not substantially closed. The method includes mounting a biasing element on the leaflet and applying magnetic force to the element to force the leaflet to the closed position before the valve experiences a negative pressure transient of 700 mmHg. More preferably, the leaflet is moved to the closed position before the valve experiences a negative pressure transient of 500 mmHg. Even more preferably, the leaflet is closed before the valve experiences a negative pressure transient of 250 mmHg. More preferably still, the leaflet is closed before the valve experiences a negative pressure transient of 100 mmHg.

In general, in another aspect, the invention features a replacement heart valve that includes a valve body and a leaflet mounted in the body for pivoted rotation about an axis between open and closed positions. The leaflet does not impact against a stop in the open position.

Other advantages and features will become apparent from the following description and from the claims.

BRIEF DESCRIPTION OF THE DRAWING

FIG. 12 is a schematic cross-sectional view of the heart valve prosthesis.

FIG. 12A is a fragmentary sectional view, on an enlarged scale, of a heart valve prosthesis with a further modified main body structure.

FIG. 13 is an enlarged fragmentary sectional view taken along line 13—13 of FIG. 12 and showing a part of the construction of the mounting ear and its associated recess.

FIG. 14 is an enlarged fragmentary perspective view showing a leaflet ear.

FIG. 15 is a fragmentary perspective view showing a leaflet ear.

DESCRIPTION OF THE PREFERRED EMBODIMENTS

Figure 1:
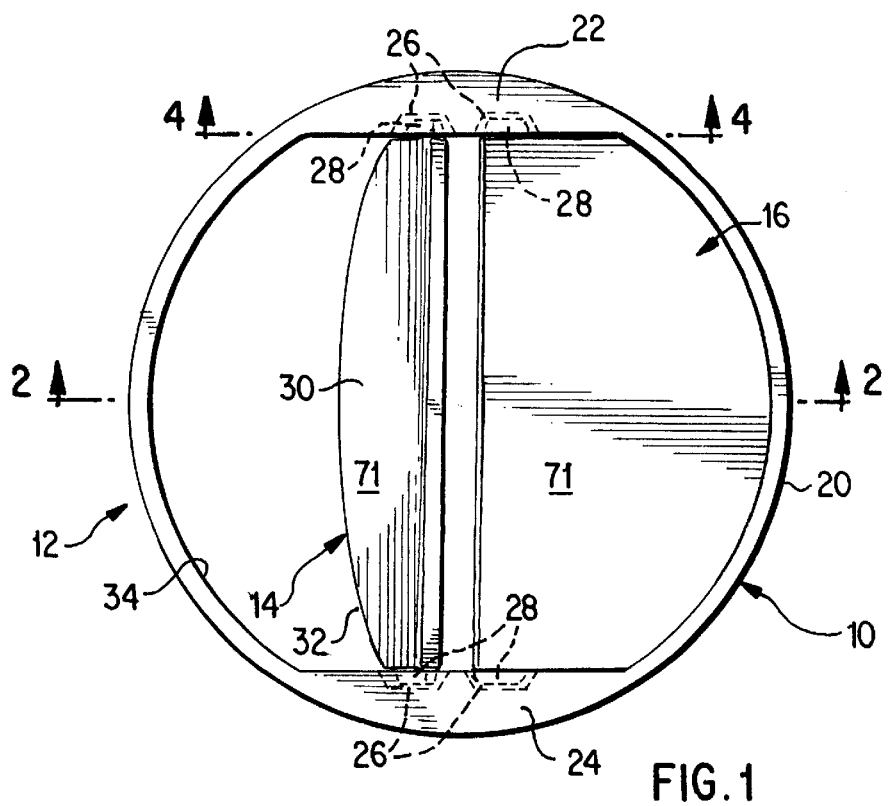
FIG. 1 is a top plan view of a heart valve prosthesis.

Referring to FIG. 1, a tilting, bileaflet heart valve prosthesis 10 has two pivotally mounted rigid leaflets 14 and 16 that regulate the flow of blood through a central passageway of the prosthesis 10. As used in this context, "rigid" means that the leaflet does not flex substantially in use. In preferred embodiments, the rigid leaflets comprise pyrolytic carbon. In response to aortic pressure and contractions of the heart, each leaflet 14, 16 is constructed to pivot to open and close a different half of the central passageway. When blood pressure rises in response to a contraction of the heart, the resultant pressure on an inflow face 71 of the leaflet 14, 16 forces the leaflet 14, 16 to pivot from a closed position to a fully open position which permits blood to flow through the central passageway.

When the contraction is complete, the blood pressure drops until an equilibrium condition is reached in which the blood pressure on the inflow face 71 matches the blood pressure on an outflow face 73 (see FIG. 2) of the leaflet 14, 16. Eventually, in response to pressure from the aorta on the outflow face 73, the leaflet 14, 16 pivots back to the closed position to complete one full cycle of the prosthesis 10.

The leaflet will shut forcefully with a violent negative pressure transient, if unmodified, when the pressure across the leaflet reverses. Such abrupt, forceful closure may damage the blood and give rise to increased thrombosis risk.

Figure 2:
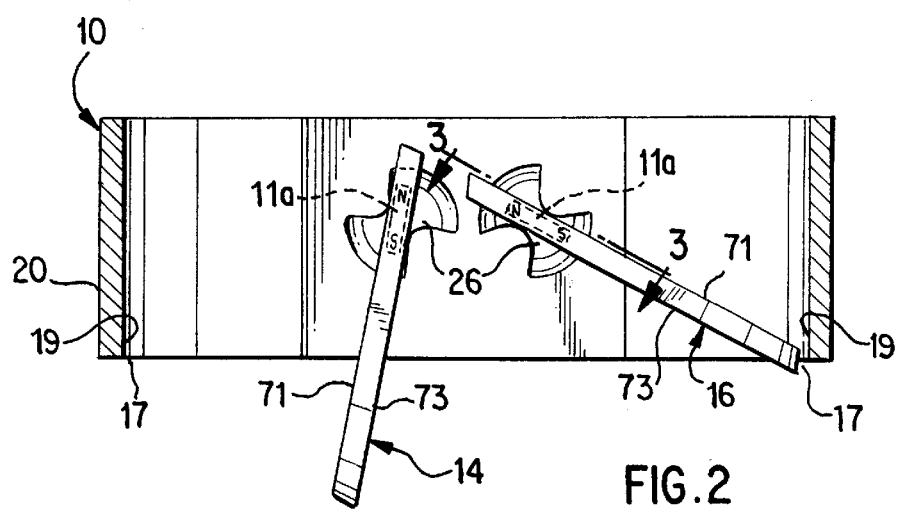
FIG. 2 a cross-sectional view taken along line 2—2 of FIG. 1.
Figure 3:
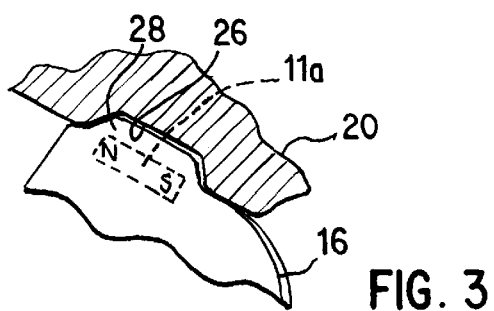
FIG. 3 is a fragmentary cross-sectional view taken along line 43 of FIG. 2.

Referring to FIG. 2, the prosthesis 10 of the present invention uses a biasing force, such as a magnetic force to move each rigid leaflet 14, 16 to a closed position 19 sufficiently early in the cardiac cycle to prevent a negative pressure transient of 700 mmHg or great from occurring. More preferably, the valve is closed sufficiently early to avoid a negative pressure transient of 500 mmHg or greater from occurring. Even more preferably, the valve is closed sufficiently early to avoid a negative pressure transient of 250 mmHg or greater from occurring. More preferably still, the valve is closed sufficiently early in the cardiac cycle to prevent a negative pressure transient of 100 mmHg or greater from occurring. This may be achieved, in particular, by moving the leaflet to the closed position 19 during the equilibrium condition when no other forces affect the position of the leaflet 14, 16. Thus, when the aortic pressure increases and the velocity of the flow of blood decreases the leaflets begin to close before the direction of blood flow reverses, so the leaflet 14, 16 is in a closed position when the direction of blood flow is reversed. As a result of this bias toward the fully closed position, exposure of the blood to transients is substantially reduced or eliminated. The leaflets 14 and 16 are also not subjected to substantial bending strains, impact loading is reduced, the amount of blood that flows in a retrograde direction during closing is substantially reduced or eliminated, resulting in a more efficient valve, and the valve closure sound is significantly reduced. Similarly, the possibility of fatigue failure of the leaflets 14 and 16 is reduced or minimized and damage to the blood is also reduced or minimized.

Figure 4:
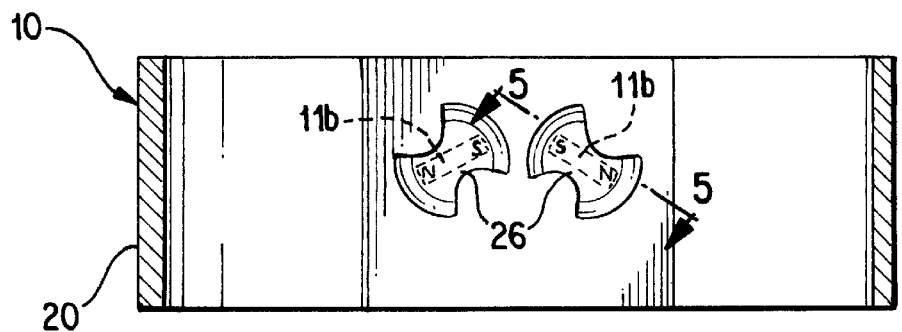
FIG. 4 is a cross-sectional view taken along line 4—4 of FIG. 4.
Figure 5:
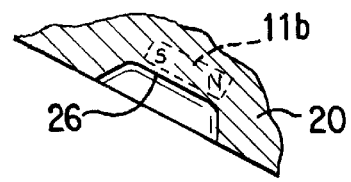
FIG. 5 is a fragmentary cross-sectional view taken along line 5—5 of FIG. 4.

Attractive and/or repulsive magnetic forces may be used to move the leaflet 14, 16 to the closed position. In some embodiments, as shown in FIG. 2, the prosthesis 10 may include a pair of leaflet magnets 11a and associated body magnets 11b. The magnets may be permanent magnets or electromagnets. Each leaflet magnet 11a is embedded in the leaflet 14, 16 near a pivotal connection between the leaflet 14, 16 and an annular body 20 (defining the central passageway) of the prosthesis 10. For each leaflet magnet 11a, an associated body magnet 11b is embedded in the body 20 near the pivotal connection, as shown in FIG. 4. Each body magnet 11b interacts with its associated leaflet magnet 11a to exert force on the leaflet 14, 16 to move the leaflet 14, 16 toward the closed position, and preferably to the closed position, even before the pressures exerted by the blood on the inflow 71 and outflow 73 faces are substantially equal.

Each leaflet magnet 11a is generally coplanar with the leaflet 14, 16. The magnetic axis of the leaflet magnet 11a extends radially outward from the pivotal axis of the leaflet 14, 16 toward the free end of the leaflet 14, 16, and the south pole of the magnet 11a is closer to the free end than the north pole. Each body magnet 11b is generally tangential to the central passageway of the body 20.

Each leaflet 14, 16 is pivotally connected to the body 20 at two diametrically opposed pivotal connection points. Although only one pivotal connection between each leaflet 14, 16 and the body 20 is shown and described below, the valve prosthesis 10 is symmetrical, and similar arrangements of magnets surround the other pivotal connections. However, in some embodiments, the valve may be asymmetrical. Thus, in these asymmetrical embodiments, magnets may not surround all of pivotal connections between the leaflet and the body of the valve prosthesis.

At each pivotal connection point, an ear 28 of the leaflet 14, 16 is constructed to rotate inside an orifice, or recess 26, formed in the body 20. Referring to FIGS. 2–5, for each recess 26, one body magnet 11b is embedded in the body 20 behind the recess 26, and the associated leaflet magnet 11a is embedded in the ear 28 that rotates inside the recess 26. Although the relative magnetic orientations of the magnets 11a and 11b change as the leaflet 14, 16 rotates, the distance between the magnets 11a and 11b remains approximately the same. However, in other embodiments, the leaflet 11a and body 11b magnets are embedded elsewhere. For example, each leaflet magnet 11a may be embedded in the free end of the leaflet 14, 16, and the associated body magnet 11b may be embedded in the body 20 near the fully closed position of the leaflet.

In the valve prosthesis 10, the magnets 11a and 11b are spatially oriented to maximize the magnetic attraction between the magnets 11a and 11b when the leaflet 14, 16 is in the partially closed position 17. In this manner, when the leaflet 14, 16 is closed, the magnetic axes of the magnets 11a and 11b are oppositely aligned, i.e., the north pole of the leaflet magnet 11a is near the south pole of the associated body magnet 11b, and the south pole of the leaflet magnet 11a is near the north pole of the associated body magnet 11b.

When the heart contracts, forward blood flow through the valve 10 causes the leaflets 14 and 16 to open. As the magnitude of the forward flow decreases, the attractive forces caused by the interaction of opposite poles of the magnets 11a and 11b draws each leaflet 14, 16 back toward the closed position 17. As a result of this bias introduced by the magnets 11a and 11b, upon reversal of the flow direction, the leaflets 14 and 16 have preferably already pivoted to the closed position. Thus, the bias supplied by the magnets prevents the leaflets 14, 16 from slamming shut as the pressure across the valve reverses, and also prevents exposure of the blood to closing pressure transients.

Figure 6:
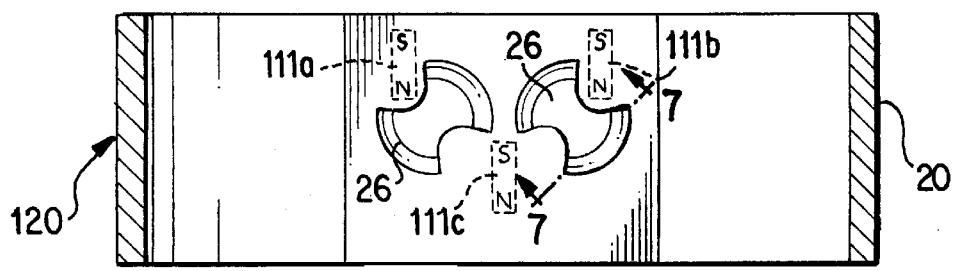
FIG. 6 is a cross-sectional view of the body of another heart valve prosthesis.
Figure 7:
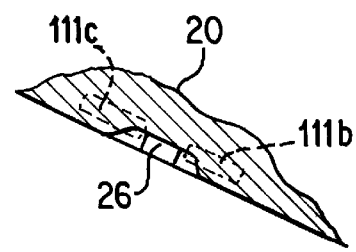
FIG. 7 is a fragmentary cross-sectional view taken along line 7—7 of FIG. 6.

Referring to FIGS. 6 and 7, in another embodiment, a heart valve prosthesis 120 is constructed to use both attractive and repulsive magnetic forces to move the leaflet 14, 16 to the closed position 19. On each diametrically opposed side of the body 20, three body magnets 111a, 111b and 111c embedded in the body 20 behind the recesses 26 replace the two body magnets 11b. Like the spatial arrangement of the body magnets 11b of the prosthesis 10, the body magnets 111a, 111b and 111c are generally tangential to the central passageway of the body 20. As compared to the prosthesis 10, the spatial and magnetic orientations of the leaflet magnets 11a are unchanged in the prosthesis 120.

Two of the outer body magnets 111a and 111b attract the leaflets 14 and 16, respectively, to the closed position 19. The north poles of the outer body magnets 111a and 111b are positioned near where the south pole of the leaflet magnets 11a rest when the leaflets 14 and 16 are in the closed positions 19.

The center body magnet 111c is spatially arranged so that the body magnet 111c repels the two leaflet magnets 11a when both leaflets 14 and 16 are fully open. In this manner, the south pole of the magnet 111c is near the south poles of the leaflet magnets 11a when the leaflets 14 and 16 are fully open. As a result of this arrangement, the leaflets 14 and 16 stay fully open only during the period of peak forward flow through the valve prosthesis 120. In other embodiments, if less force is required, then either the center magnet 111c or the two outer magnets 111a and 111c may be removed.

Figure 8:
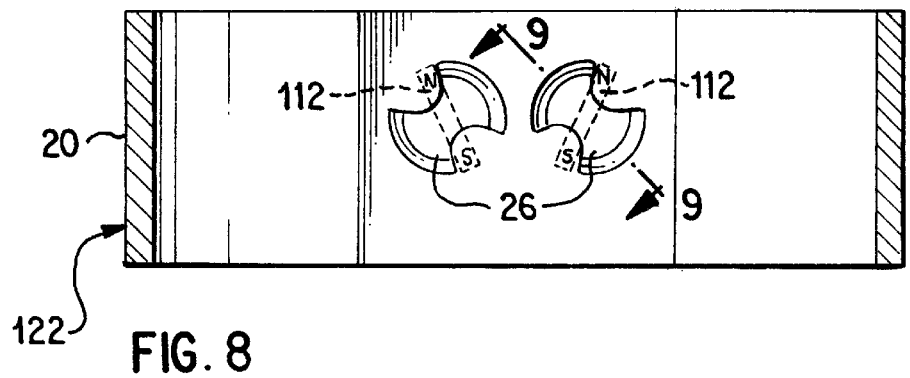
FIG. 8 is a cross-sectional view of the body of another heart valve prosthesis.
Figure 9:
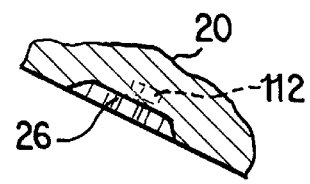
FIG. 9 is a fragmentary cross-sectional view taken along line 9—9 of FIG. 6.

Referring to FIGS. 8 and 9, in another embodiment, magnets 112 of a heart valve prosthesis 122 are arranged to increase the opening resistance of the leaflet 14, 16 as the opening angle of the leaflet 14, 16 increases. To accomplish this, the prosthesis 122 has body magnets 112 that are embedded in the body 20 and replace the body magnets 11b of the prosthesis 10. Like the body magnets 11b, the body magnets 112 are generally tangential to the central passageway of the body 20. As compared to the prosthesis 10, the spatial and magnetic orientations of the leaflet magnets 11a are unchanged in the prosthesis 122.

Each body magnet 112 is associated with one of the leaflet magnets 11a and is spatially arranged to use a repulsive magnetic force to return the leaflet 14, 16 to the closed position. To accomplish this, each pole of the body magnet 112 is positioned so that each pole of the body magnet 112 is near the opposite pole of the associated leaflet magnet 11a when the leaflet 14, 16 is in the fully open position. Another advantage of this arrangement is that both poles of associated magnets are in opposition so more force is generated by fewer magnets.

Figure 10:
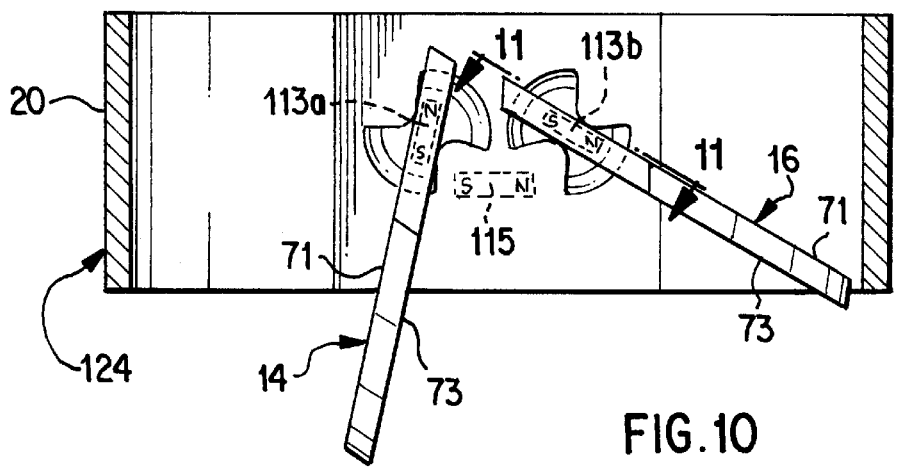
FIG. 10 is a cross-sectional view of the body of another heart valve prosthesis.
Figure 11:
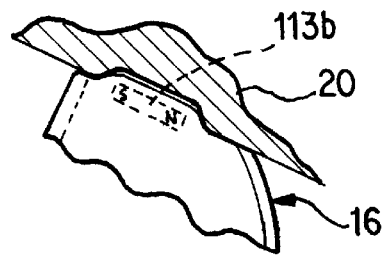
FIG. 11 is a fragmentary cross-sectional view taken along line 11—11 of FIG. 10.

Referring to FIGS. 10 and 11, in another embodiment, a heart valve prosthesis 124 uses repulsive magnetic forces to close the leaflets 14 and 16. In the heart valve prosthesis 124, the leaflet magnets 11a of the prosthesis 10 are replaced by leaflet magnets 113, and for each diametrically opposed side of the body 20, the pair of body magnets 11b of the prosthesis 10 are replaced by one body magnet 115.

Similar to the position of the leaflet magnets 11a, each leaflet magnet 113 is generally coplanar with the leaflet 14, 16, and the magnetic axis of the leaflet magnet 113 extends radially outward from the pivotal axis of the leaflet 14, 16 toward the free end of the leaflet 14, 16. The south pole of the magnet 113a is closer to the free end of the leaflet 14, 16 than the north pole of the magnet 113a. In contrast, the north pole of the magnet 113b is closer to the free end of the leaflet 14, 16 than the south pole of the magnet 113b.

The body magnet 115 is generally tangential to the central passageway of the body 20 and spatially oriented so that when the leaflets 14 and 16 are in the fully open position, the poles of the body magnet 115 are near (and thus, repelled by) like poles of the leaflet magnets 113a and 113b.

Referring back to FIG. 1, the heart valve prosthesis 10 has three major components: the body 20 and the leaflets 14 and 16. The prosthesis 10 has a plane of symmetry extending through its midsection and generally vertically as shown in FIGS. 1 and 12.

The sidewall of the body 20 has a pair of oppositely disposed formations 22, 24 of increased thickness and in which adjacent pairs of recesses 26 are formed. Each of the recesses 26 receive an associated ear 28 on the end portion of a valve leaflet 14, 16. The recesses 26, act as seats for the ears 28 of the leaflets 14, 16 and since the recesses 26, ears 28, and leaflets 14, 16 are all substantially identical to their counterpart, only one of each will be described in detail.

The left hand leaflet 14 is shown to include a principal leaflet body portion 30 having a curvilinear exterior edge 32 which is beveled so as to form a fluid-tight fit with a radially inwardly directed surface 34 on the curvilinear portion of valve body 20. The leaflet 14 also contains a beveled, generally planar center edge surface 36 adapted, in the closed position of the leaflet 14 to mate with a counterpart surface (not shown in detail) on the adjacent leaflet 16. The surface 36 extends transversely to the cylindrical axis of the body 20.

Mounting of the valve ears is achieved by a combination of three features, one being the provision of the ear 28 for example, on the leaflet 14. This ear 28 (see FIG. 14) includes a top surface portion 40 of generally trapezoidal shape when shown in plan view and being defined by an outermost, vertically extending end surface 42, and opposed diagonally extending, contoured surfaces 44, 46. These surfaces 44, 46 are frustoconical surfaces of revolution about the axis of pivoting movement of the leaflets 14, 16 and extend between the top ear surface 40 and the bottom ear surface 48.

As shown, the surfaces 44, 46 would be truly frustoconical if the product of full revolution but, being surfaces of only partial revolution, subtend only a slight angle rather than a full 360 degree angle.

Each ear 28 is received in use within one of the plurality of contoured valve ear seating recesses 26, a description of only one of which is believed necessary to an understanding of the invention. Thus, referring again to one of such recess 26, as shown in FIG. 15, this element includes a flat end wall or endface surface 54, a pair of opposed, truncated frustoconical or beveled sidewall surfaces 56, 58 and horizontally extending rounded ear support or seating surfaces 60, 62.

The end face surface 54 serves as an end play limiting surface, and the opposed beveled side wall surfaces, 56, 58 serve as guide surfaces which determine the arcuate movement of the ears 28. The support, or seating surfaces 60, 62, support the leaflet ears against dynamic ear movement caused by blood flow rather than support against movement in response to gravity only.

Likewise, the ear surfaces 44, 46 serve as guide surfaces, the top and bottom ear surfaces 40, 48 as support surfaces, and the end face surface 42 as an end play limiting surface.

In the operation of the assembled valve 110, each of the leaflets 14, 16 are supported from time to time by various surfaces during the pivoting movement. Thus, the rounded seat surface 60 extends horizontally and faces upwardly to support the opposable facing lower ear surface 48 when there is an overall downward force acting on the leaflet. As the leaflet swings to an open position, it continues to rest on a portion of the support surface 60, and is guided in its arcuate path as it opens pivotally by contact, interference, or near-contact between the frustoconical surfaces 44, 46 for example, on the ear 28, and the counterpart tapered or bevelled surfaces 56, 58 forming parts of the recess 26.

When the valve leaflet 14 is fully closed and is acted upon by a net pressure coming from the downstream side or from beneath the valve as shown in FIG. 12, resistance to axial displacement is provided by engagement between a part of the downwardly directed ear seating surface 62 and the upwardly directed surface 40 on the valve leaflet ear 28. This movement involves a rolling and sliding pivot action between the surfaces 40 and 62 rather than a rocking action over a single pivot point. End play is restricted within permissible limits by engagement of the respective end wall surfaces 50 on the ear 28 and the surface 55 of the inside orifice wall, as was the case in valve opening. Side play is restricted by engagement of the ear surfaces 44, 46 and the recess tapered surfaces 56, 58 as well.

Consequently, in use, where there is a pressure from above, as in FIG. 12, the left hand valve leaflet 14 tends to open, inasmuch as a greater portion of its surface area lies to the left of its pivot axis than to the right thereof. In opening, the valve unseats by disengagement of both the cylindrical surfaces 32, 34 and the rectilinear center transverse surfaces 36. During this action, the ear and recess surfaces just described combine to guide the ears 28 and their leaflet 14 through a limited range of arcuate movement. By reference to the phantom line position of the leaflet 14 in FIG. 12, it will be noted that excess leaflet movement is limited by the contour of the recesses whose surfaces 60, 62 prevent undue opening, while movement beyond desired limits is also prevented by engagement of the beveled surface 32 and inner leaflet edge 36, with cylinder wall 34 and the inner counterpart edges of the opposing leaflet 16, respectively.

Figure 18:
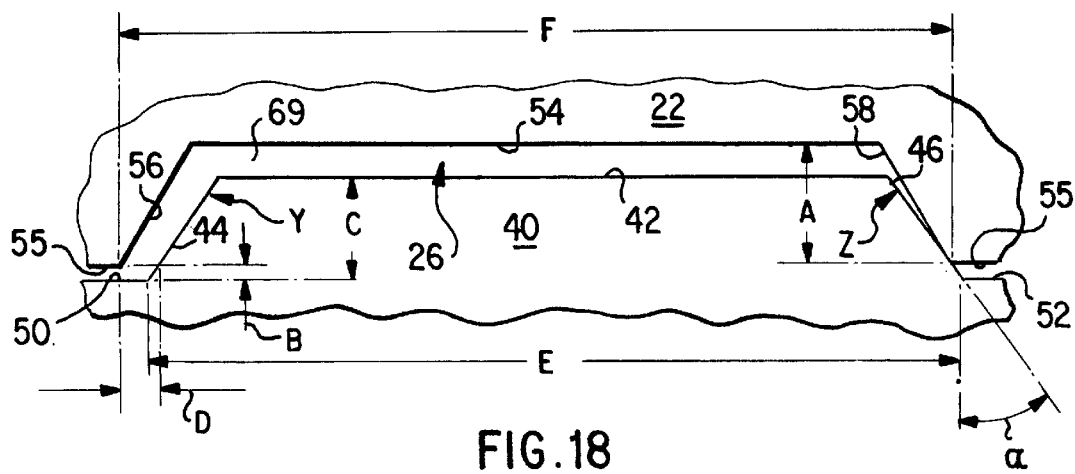
FIG. 18 is a diagrammatic view of certain constructional features of the ear and recess parts of the valve prosthesis.

Referring to FIG. 18, the leaflet ears are formed as conic section surfaces which are truncated in perpendicular planes. In the case of the leaflet ears 28, and in the case of the well or recess 26, contoured surfaces, including substantially flat end face surfaces 42 and frustoconical side walls 44, 46 are received in a recess 26 of desired shape. This permits arcuate movement of the valve leaflet while carefully controlling and limiting end play and side play, or misalignment.

As will be noted from FIG. 18, in a well or recess having an entrance diameter F, an ear having a maximum width of E may be inserted and retained. The depth A of the recess is slightly greater than the height C of the ear.

In one embodiment, the valve body is made from a metal material instead of a ceramic material. Accordingly, there are shown herein both ceramic and metalcontaining valve bodies.

Thus, referring to FIG. 12A, there is shown an enlarged fragmentary section of the side wall portion 20a of the valve 10. This shows that the side wall may itself be composed of a graphite body 100 having a coating 102 of Pyrolyte carbon.

Figure 16:
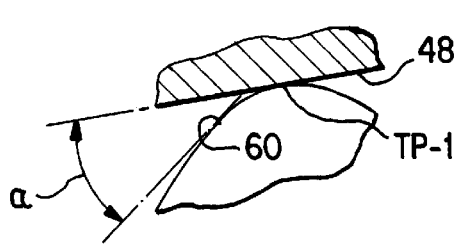
FIG. 16 is a schematic view showing details of the rocking movement of the leaflet mounting ear in a given position.
Figure 17:
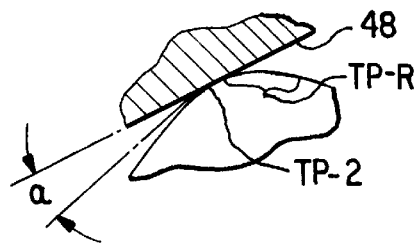
FIG. 17 is a schematic view showing the recess and ear of FIG. 16 in another position.

Referring to FIGS. 16 and 17, as the tangent point TP between the lower ear surface 48 and the upwardly facing recess ear seat surface 60 moves between positions TP-1 (FIG. 16) and TP-2 (FIG. 17), there is a broad range of contact or tangent points TP-R rather than the single tangent or fulcrum pivot point, along which the leaflet is supported.

This "washes" the surface, spreads out the area of contact and, it is believed, diminishes possible red cell damage or crushing, and permits a floating action which extends wear.

While not specifically shown in FIGS. 16 and 17, it will be understood that a similar rolling action or moving of tangent or contact points occurs in respect to the upper ear surface 40 and the lower recess ear support or seat surface 62. The leaflet ears are thus alternately pivoting about and/or being supported by first a lower surface 60 and then an upper surface 62 of the recess 26, respectively engage downwardly 20 and upwardly directed surfaces 48, 40 on the leaflet ear 28.

The simplicity of the pivotal leaflet valve action provides support and facing surfaces in the respective ear-receiving recesses sufficient to control the valve leaflet movement, and to reduce wear by reducing slop and providing a rolling action around a rounded pivot rather than localizing wear. Moreover, the configuration of a frustoconical pivot action guide surfaces on both the ear and in the recess, with these surfaces being related such that the well or recess is steeper or has an included angle less than that of the ears of the leaflet provides a potential for greatly extended wear and reliability in a highly critical environment.

Figure 19:
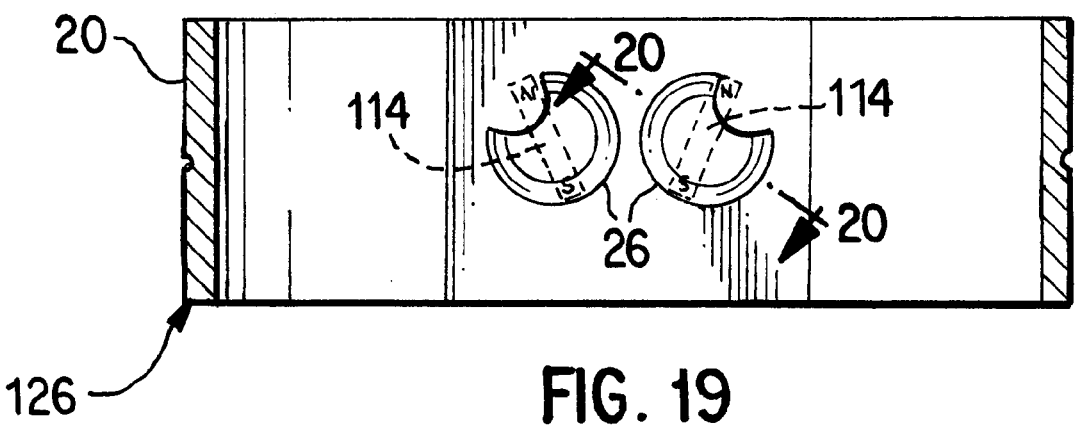
FIG. 19 is a cross-sectional view of the body of another heart valve prosthesis.
Figure 20:
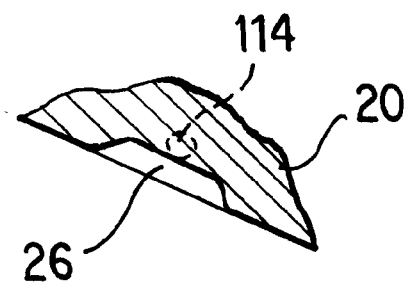
FIG. 20 is a fragmentary cross-sectional view taken along line 20—20 of FIG. 19.

Referring to FIGS. 19 and 20, in another embodiment, a heart valve prosthesis 126 does not have the stop 60 in each recess 26 to constrain the pivotal freedom of the leaflet 14, 16 and define the maximum open angle of the leaflet 14, 16. Instead, to define the maximum open angle of the leaflet 14, 16, the heart valve prosthesis 126, similar in design to the prosthesis 122 (see FIGS. 8 and 9), has body magnets 114 that have the same spatial and magnetic orientation as the body magnets 112. However, unlike the body magnets 112, the body magnets 114 exert sufficient force on the leaflet magnets 11a to keep each leaflet 14, 16 from pivoting past a position that is aligned with the magnetic axis of the body magnet 114. As a result of the elimination of the stop 60, stasis regions within the recess 26 may be substantially or completely eliminated.

Figure 21:
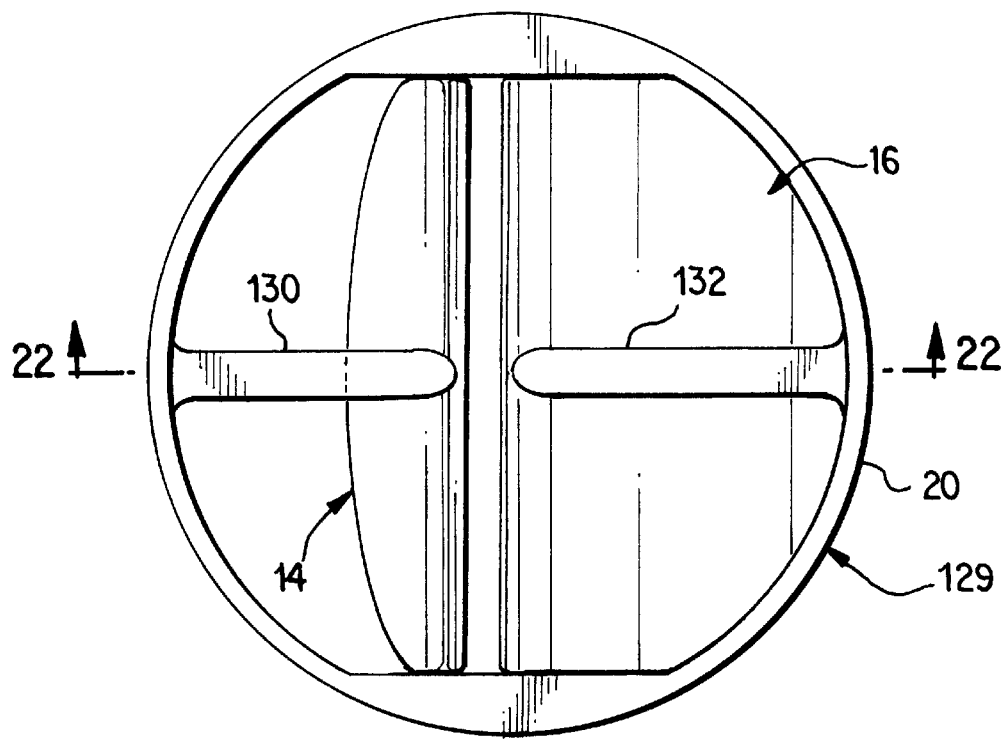
FIG. 21 is a top plan view of another heart valve prosthesis.
Figure 22:
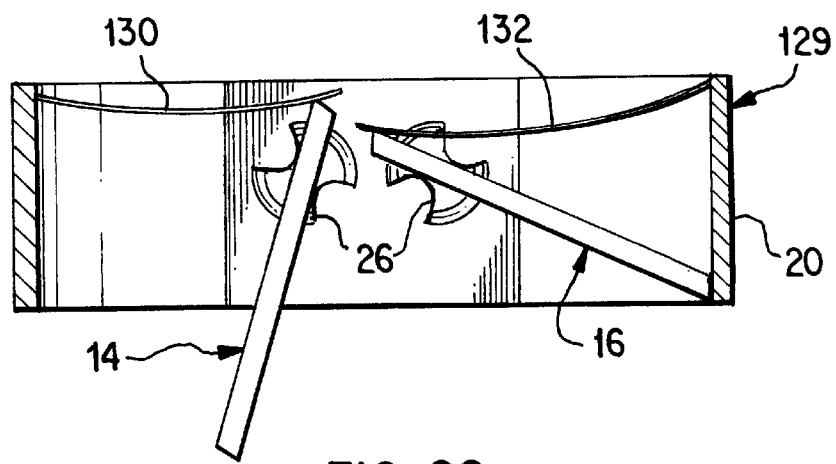
FIG. 22 is a cross-sectional view taken along line 22—22 of FIG. 21.

Other biasing mechanisms may be used to move the leaflet 14, 16 back to the closed position. For example, referring to FIGS. 21 and 22, in a heart valve prosthesis 129, the magnets are replaced by resilient leaf springs 130 (for the leaflet 14) and 132 (for the leaflet 16). Each spring 130, 132 is orthogonal to the pivotal axis of the leaflet 14, 16 and has one end secured to the body 20. From the body 20, the spring 130, 132 extends across the inflow opening of the prosthesis 129 (and over the leaflet 14, 16) to contact the leaflet 14, 16 near the leaflet's pivotal axis. Due to this arrangement, the spring 130, 132 exerts increasing force on the leaflet 14, 16 as the leaflet 14, 16 opens. As a result, the leaflet 14, 16 returns to the closed position sufficiently early in the cardiac cycle to prevent a negative pressure transient of 700 mmHg or great from occurring. More preferably, the valve is closed sufficiently early to avoid a negative pressure transient of 500 mmHg or greater from occurring. Even more preferably, the valve is closed sufficiently early to avoid a negative pressure transient of 250 mmHg or greater from occurring. More preferably still, the valve is closed sufficiently early in the cardiac cycle to prevent a negative pressure transient of 100 mmHg or greater from occurring. The spring 130, 132 may be formed from many different materials, such as metal or plastic.

Other embodiments are within the scope of the following claims. For example, the biasing mechanisms may be used in other types of valve prostheses, such as a polymer valve prosthesis or a trileaflet valve prosthesis. However, it is preferred that at least a portion of the leaflets comprise pyrolytic carbon. The heart valve prosthesis may include a combination of at least one spring and at least one magnet. Not all pivotal connections between the leaflet and the body may include magnets. In addition, the magnetic attraction between a magnet and an unmagnetized piece of metal can be used instead of using two magnets.

What is claimed is:

1. A heart valve prosthesis for implantation within the heart of a patient, said valve comprising:
   an annular body having a fluid passageway, an upstream side and a downstream side;
   at least one leaflet pivotally mounted in the fluid passageway of the body, said leaflet being movable between a closed position wherein said fluid passageway is substantially closed and an open position wherein said fluid passageway is not closed, said valve being characterized by a pressure transient at said upstream side immediately following movement to the closed position when implanted in a patient;
   a first magnet coupled to the leaflet; and
   a second magnet coupled to the body and configured to interact with the first biasing element to exert a force on the leaflet to move the leaflet to the closed position such that said pressure transient is less that 250 mmHg.

2. The heart valve prosthesis of claim 1 wherein the first and second magnets are further configured to move the leaflet to the closed position when a first fluid pressure exerted on an inflow surface of the leaflet is greater than a second fluid pressure exerted on an outflow surface of the leaflet.

3. The heart valve prosthesis of claim 1 wherein the first and second magnets are configured to attract each other when the leaflet is in the closed position.

4. The heart valve prosthesis of claim 1 wherein the prosthesis comprises a bileaflet mechanical heart valve prosthesis.

5. A heart valve prosthesis comprising:
   an annular body having a fluid passageway therethrough;
   at least one rigid leaflet pivotally mounted in the fluid passageway of the annular body and movable between a closed position wherein said fluid passageway is substantially closed and an open position wherein said fluid passageway is not closed;
   a first magnet coupled to the leaflet, and a second magnet coupled to said body, said first and second magnets cooperating to exert a biasing force to bias said leaflet to the closed position, and wherein said first and said second magnets are configured to attract each other when the leaflet is in the closed position, and to repel each other when the leaflet is in the open position.

6. The heart valve prosthesis of claim 5 wherein the heart valve prosthesis comprises a mechanical bileaflet heart valve prosthesis.

7. A heart valve prosthesis comprising:
   an annular body having a fluid passageway therethrough;
   at least one rigid leaflet pivotally mounted in the fluid passageway of the annular body and movable between a closed position wherein said fluid passageway is substantially closed and an open position wherein said fluid passageway is not closed;
   a first magnet coupled to the leaflet, and a second magnet coupled to said body, said first and second magnets cooperating to exert a biasing force to bias said leaflet to the closed position, wherein said first and said second magnets are configured to attract each other when the leaflet is in the closed position, the open position defines a predetermined maximum angular position of the leaflet, and the first and second magnets are configured to prevent the leaflet from traveling substantially beyond the maximum angular position.

8. A heart valve prosthesis for implantation within the heart of a patient, said valve comprising:
   an annular body having a fluid passageway, an upstream side and a downstream side;
   at least one leaflet pivotally mounted in the fluid passageway of the body, said leaflet being movable between a closed position wherein said fluid passageway is substantially closed and an open position wherein said fluid passageway is not closed, said valve being characterized by a pressure transient at said upstream side immediately following movement to the closed position when implanted in a patient;
   a first biasing element mounted to the leaflet; and
   a second biasing element mounted to the body and configured to interact with by the first biasing element to exert a force on the leaflet to move the leaflet to the closed position such that said pressure transient is less than 250 mmHg,
   wherein the first and second biasing elements are configured to repel each other when the leaflet is in the open position.

9. A heart valve prosthesis for implantation within the heart of a patient, said valve comprising:
   an annular body having a fluid passageway, an upstream side and a downstream side;
   at least one leaflet pivotally mounted in the fluid passageway of the body, said leaflet being movable between a closed position wherein said fluid passageway is substantially closed and an open position wherein said fluid passageway is not closed, said valve being characterized by a pressure transient at said upstream side immediately following movement to the closed position when implanted in a patient;

a first biasing element mounted to the leaflet; and a second biasing element mounted to the body and configured to interact with the first biasing element to exert a force on the leaflet to move the leaflet to the closed position such that said pressure transient is less than 250 mmHg, wherein the open position defines a predetermined maximum angular position of the leaflet, and the first and second biasing elements are configured to prevent the leaflet from traveling substantially beyond the open position.

10. A method for use of a heart valve prosthesis for implantation within the heart of a patient, said prosthesis having a fluid passageway with an upstream side and a downstream side, and at least one leaflet located in the passageway, the leaflet being movable between a closed position wherein the fluid passageway is substantially closed and an open position wherein the fluid passageway is not substantially closed, said valve being characterized by a pressure transient at said upstream side following movement to the closed position after implantation in a patient, the method comprising:

mounting a first magnet on the leaflet; and applying magnetic force to the first magnet to force the leaflet to the closed position such that said pressure transient is less than 250 mmHg.

* * * * *